(12) United States Patent
Diaz

(10) Patent No.: US 7,879,374 B2
(45) Date of Patent: Feb. 1, 2011

(54) COMPOSITION INCLUDING SUPEROXIDE DISMUTASE AND PRICKLY-PEAR CACTUS FOR MINIMIZING AND PREVENTING HANGOVERS

(75) Inventor: Victor H. Diaz, Aventura, FL (US)

(73) Assignee: Cellutions, LLC, Plantation, FL (US)

( * ) Notice: Subject to any disclaimer, the term of this patent is extended or adjusted under 35 U.S.C. 154(b) by 52 days.

(21) Appl. No.: 11/493,480

(22) Filed: Jul. 24, 2006

(65) Prior Publication Data

US 2008/0020071 A1 Jan. 24, 2008

Related U.S. Application Data

(60) Provisional application No. 60/701,568, filed on Jul. 22, 2005.

(51) Int. Cl.
*A61K 36/00* (2006.01)
(52) U.S. Cl. .................... 424/767; 424/725
(58) Field of Classification Search ............ None
See application file for complete search history.

(56) References Cited

U.S. PATENT DOCUMENTS

| | | | |
|---|---|---|---|
| 1,379,149 A * | 5/1921 | Wichmann | 524/71 |
| 2,980,587 A * | 4/1961 | Ham et. al. | 426/73 |
| 4,496,548 A | 1/1985 | Moldowan et al. | |
| 4,703,045 A | 10/1987 | Guinot | |
| 5,296,241 A | 3/1994 | Brimberg et al. | |
| 5,538,878 A * | 7/1996 | Thomas et al. | 800/288 |
| 5,922,346 A | 7/1999 | Hersh | |
| 6,228,347 B1 | 5/2001 | Hersh | |
| 6,365,198 B1 | 4/2002 | Niazi | |
| 6,447,820 B1 | 9/2002 | Niazi | |
| 6,451,341 B1 | 9/2002 | Slaga et al. | |
| 6,713,091 B1 | 3/2004 | Kim | |
| 6,846,494 B1 | 1/2005 | Verheul-Koot et al. | |
| 2001/0043956 A1 | 11/2001 | Mirza et al. | |
| 2003/0008058 A1 | 1/2003 | Ariga et al. | |
| 2004/0082667 A1 | 4/2004 | McCadden et al. | |
| 2005/0003030 A1 * | 1/2005 | Simon et al. | 424/769 |
| 2006/0269535 A1 * | 11/2006 | Naidu et al. | 424/94.1 |

FOREIGN PATENT DOCUMENTS

WO WO 03/037324 A1 5/2003

OTHER PUBLICATIONS

Dr. Duke's Phytochemical and Ethnobotanical Databases; Opuntia ficus-indica L., URL<http://www.ars-grin.gov/cgi-bin/duke/farmacy2.pl> pp. 1-4, accessed May 7, 2008.*
Dr. Duke's Phytochemical and Ethnobotanical Databases; Salix alba L. (White Willow): URL<http://www.ars-grin.gov/cgi-bin/duke/farmacy2.pl, pp. 1-4, accessed on May 7, 2008.*
"Opuntia (Prickly Pear), 250 mg—100 caps," HerbalRemedies.com, http://www.herbalremedies.com/14050.html, printed Jul. 24, 2006, 1 page.
"Chaser™ Hangover Pills," Chaser, http://www.chaserpills.net/?a=fargo&c=0, 2 pages, printed Jul. 24, 2006.
"S.O.D. 2000 Plus™," All in One, http://www.allinnone.com/vitamins/product-skew-712.html, 2 pages, printed Jul. 24, 2006.

* cited by examiner

*Primary Examiner*—Patricia Leith
(74) *Attorney, Agent, or Firm*—Assouline & Berlowe, P.A.; Loren Donald Pearson

(57) ABSTRACT

A composition including superoxide dismutase (SOD) and prickly pear cactus (OFI) protects against, minimizes the effects of, and hastens recovery from the typical symptoms associated with an alcohol induced hangover. In addition, sesamin and alpha-lipoic acid work with the SOD and OFI for enhanced antioxidant and therapeutic effects. Thiamine, niacin, vitamin B6, folate, vitamin B12, pantothenic acid, milk thistle seed extract, flower pollen extract, eleuthero root extract, guggulsterones EZ, white willow bark extract, sclareolide, *ginkgo biloba* extract, caffeine, and *boswellia serrata* extract can be added to the composition for additional treatment of symptoms.

23 Claims, No Drawings

COMPOSITION INCLUDING SUPEROXIDE DISMUTASE AND PRICKLY-PEAR CACTUS FOR MINIMIZING AND PREVENTING HANGOVERS

CROSS-REFERENCE TO RELATED APPLICATIONS

This application claims the benefit of U.S. Provisional Application No. 60/701,568, filed Jul. 22, 2005.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

The invention relates to compositions for protecting against, minimizing, and hastening recovery from the typical symptoms associated with an alcohol induced hangover.

2. Description of Related Art

An alcohol hangover is associated with a variety of symptoms that may include dehydration, tiredness, headache, nausea, diarrhea, weakness, difficulty concentrating, anxiety, irritability, sensitivity to light and noise and trouble sleeping. The symptoms vary from person to person, and occasion to occasion, usually beginning several hours after drinking. It is not clear whether hangovers affect cognitive abilities.

Hangovers are thought to be multi-causal. Ethanol has a dehydrating effect (such substances are known as diuretics), which causes headaches, dry mouth, and lethargy. Dehydration causes the brain to shrink away from the skull slightly. This can be mitigated by drinking water after consumption of alcohol. Alcohol's impact on the stomach lining can account for nausea. Due to the increased NADH production during metabolism of ethanol by alcohol and aldehyde dehydrogenases, excess NADH can build up and slow down gluconeogenesis in the liver, thus causing hypoglycemia.

Another factor contributing to a hangover is what results from the breakdown of ethanol via two chemical reactions, aided by enzymes produced by the cells of the liver. Ethanol is converted to acetaldehyde by the enzyme alcohol dehydrogenase, and then from acetaldehyde to acetate by the enzyme acetaldehyde dehydrogenase. Acetaldehyde and acetate are both mildly toxic, contributing to the hangover.

The two aforementioned reactions also require the conversion of NAD+ to NADH. With an excess of NADH, the lactate dehydrogenase reaction is driven to produce lactate from pyruvate (the end product of glycolysis) in order to regenerate NAD+ and sustain life. This diverts pyruvate from other pathways such as gluconeogenesis, thereby impairing the ability of the liver to supply glucose to tissues, especially the brain. Because glucose is the primary energy source of the brain, this lack of glucose contributes to hangover symptoms such as fatigue, weakness, mood disturbances, and decreased attention and concentration.

When one is drinking, the blood vessels in the face, the capillaries, will dilate, giving the person a flushed appearance, often referred to as the "drunk blush". However, when the hangover starts, the capillaries will close up again, contributing to the headache and fatigue that is often experienced in a hangover. People experiencing hangovers will often feel cold. This is because alcohol gives the person a type of hypothermia in which body heat is given off too rapidly, due to the increased blood flow to the skin.

Finally there are various nervous effects. The removal of the depressive effects of alcohol in the brain probably account for the light and noise sensitivity.

In addition, it is thought that the presence of other alcohols (such as methanol and fusel oils), by-products of the alcoholic fermentation also called congeners, exaggerates many of the symptoms; this probably accounts for the mitigation of the effects when distilled alcohol, particularly vodka, is consumed.

The amount of congeners in the drink may also have an effect. Red wines have more congeners than white wines, and some people note less of a hangover with white wine.

In alcohol metabolism, one molecule of ethanol (the primary active ingredient in alcoholic beverages) produces two molecules of NADH, utilizing Vitamin B12 as a coenzyme. Over consumption of ethanol may cause vitamin B12 deficiency as well.

Some people believe that sugar (often found in sweet cocktails) worsens hangovers.

Nicotine poisoning can often worsen hangovers, as smokers tend to smoke much more than usual while under the influence of alcohol.

Genetics also plays a part, as some people seldom, if ever, suffer hangover symptoms no matter how much they drink.

The psychosomatic nature of hangovers shouldn't be ignored either. If people expect a hangover, they tend to feel one.

Dietary supplements in liquid and capsule form have been developed in an attempt to provide relief from the aftereffects of imbibing alcohol. However, none seem to be satisfactory in providing relief.

In addition, consumers prefer an herbal supplement over a prescribed medications.

Antioxidants are substances that work by attacking free radicals. Free radicals are waste products that are created when the body turns food into energy. There are also many sources of free radicals in the environment such as ultraviolet rays, radiation, and toxic chemicals in cigarette smoke, car exhaust, and pesticides. Free radicals cause harmful chemical reactions that can damage cells in the body, making it harder for the body to fight off infections. As a result a person becomes more susceptible to long term diseases such as diabetes and liver damage.

Mirza et al. (U.S. Published Patent Application Publication US 2001/0043956 A1) discloses a hangover remedy that includes vitamin B6, charcoal, and Ephedra. The hangover remedy may be available as powder enclosed in a capsule.

Slaga et al. (U.S. Pat. No. 6,451,341) shows a formulation of vitamins and minerals that releases the vitamin and minerals over a sustained period of time. The formulation may contain vitamins A, C, E, B1, B6, and B12, as well as niacinamide, folic acid, pantothenic acid, and superoxide dismutase (SOD).

Verheul-Koot et al. (U.S. Pat. No. 6,846,494) describes a nutritional composition for the treatment of ulcers. The composition may be taken orally and may include the vitamins A, B6, and B12, as well as niacin and pantothenic acid.

Finally, the HerbalRemedies.com website offers Opuntia, or prickly pear extract, as a lone active ingredient, as a hangover remedy. Furthermore, Prickly Pear Cactus has been used in other dietary supplements. The primary disadvantage to the prior art is that Prickly Pear Cactus (OFI) by itself (as a sole active ingredient) does not provide sufficient antioxidant benefits and relief from hangover symptoms.

BRIEF SUMMARY OF THE INVENTION

It is accordingly an object of the invention to provide a composition for protecting against, minimizing the effects of, and hastening recovery from the typical symptoms associated with an alcohol induced hangover. The composition overcomes the above-mentioned disadvantages of the heretofore-known compositions of this general type.

With the foregoing and other objects in view there is provided, in accordance with the invention, a composition that includes superoxide dismutase (SOD) and prickly pear cactus.

In accordance with a further object of the invention, a composition is provided that, in addition to superoxide dismutase (SOD) and prickly pear cactus, includes sesamin. A daily dosage of sesamin in the range of 250-500 mg has been found to be effective.

In accordance with a further object of the invention, is to provide a composition that, in addition to superoxide dismutase (SOD) and prickly pear cactus, includes alpha-lipoic acid. A daily dosage of alpha-lipoic acid of 50-300 mg per day has been found to be effective.

In accordance with a further object of the invention, other ingredients can be added to the composition. These ingredients include thiamine, niacin, vitamin B6 (Pyridoxine HCl), folate (folic acid), vitamin B12, pantothenic acid, milk thistle seed extract, flower pollen extract, eleuthero root extract, guggulsterones EZ, white willow bark extract, sclareolide, *ginkgo biloba* extract, caffeine, and *boswellia serrata* extract.

The above-described compositions that include SOD and prickly pear cactus works with the body's natural defenses to enhance its ability to protect against, minimize, and help recover faster from the typical symptoms associated with an alcohol induced hangover.

The composition including superoxide dismutase and prickly pear cactus can be administered orally in the form of a gel, lozenge, tablet, gum, a powdered form in a capsule, or mixed in a liquid.

As sated, the present invention relates to a composition, which is a dietary supplement, that combines *opuntiaficus indica*, commonly referred to as prickly pear cactus, with superoxide dismutase, together with vitamins, antioxidants, and other nutrients. The dietary supplement of the present invention helps in the recovery from the symptoms associated with drinking alcohol. The dietary supplement also provides the additional benefit of providing a sustained boost of energy and helping to increase mental acuity.

The dietary supplement of the present is a unique blend of ingredients including powerful antioxidants that boost mind and body performance. The blend of ingredients also provides nutritional value for the body, and helps the body's natural defenses to accelerate the body's cleansing process and enhance its ability to efficiently metabolize alcohol in order to minimize, prevent and recover faster from the typical symptoms associated with a hangover.

Superoxide Dismutase (SOD) works by promoting the patient's antioxidant defense and immune support mechanism. By supporting the body's innate cellular protection, SOD helps to transform the most dangerous free radicals into ions that are less reactive. SOD also promotes other cells to produce more SOD, thus preparing the antioxidant defense systems against free radical attack. SOD has also been shown to play a role in reducing inflammation.

Prickly Pear Cactus extract is a type of cactus that is also known as *Opuntia ficus* indica. Although native to the United States, Mexico, and South America, the prickly pear cactus can be found throughout the world. In Mexico and the Southwest, its pulp and juice have been used to treat a numerous amount of maladies such as wounds and inflammations of the digestive and urinary tracts. Research has also shown that it has a positive effect on reducing and preventing severe hangover symptoms because of its anti-inflammatory qualities.

*Boswellia* is an herb and is also known as "Indian frankincense". *Boswellia* comes from a tree called *Boswellia Serrata*. *Boswellia* has been used for its healing properties for centuries by traditional Indian healers. Studies have identified the active anti-inflammatory ingredients within *Boswellia* known as Boswellic acids. Its anti-inflammatory properties can help alleviate the symptoms of back pain, intestinal disorders, and promote liver health.

Milk Thistle Seed Extract works as a powerful antioxidant that protects the liver from free-radical damage. Milk Thistle (also known as *Silybum Marianum*) has been used to regenerate and protect the liver from liver diseases for centuries. Milk Thistle helps fight the damaging effects of ingested toxic substances such as alcohol and those that we are exposed to in the environment. It acts by lowering the enzyme levels in the liver thus allowing for its cleansing and detoxification and most importantly the cleansing of the blood. Two of the most important antioxidants produced by the body, Glutathione and Superoxide Dismutase (SOD), are greatly enhanced by Milk Thistle. Milk Thistle is also credited for its anti-inflammatory effects.

*Ginkgo Biloba* Leaf Extract is an herbal medicine that comes from the oldest living tree species on earth. *Ginkgo* is native to China and has been used for over four-thousand years. Its healing qualities have been used to treat a variety of diseases and ailments including heart disease, depression, memory loss, and impotence. Studies also suggest that Ginkgos great benefits are due to the fact that it acts as an antioxidant, which helps promote healthy central nerve and circulatory systems. One of Ginkgos most common and popular use is as a memory booster. The mechanism is believed to be that Ginkgo increases blood flow to vital organs and tissues. This increase in blood flow allows vital organs and tissues in the body to receive more nutrients and oxygen. This in turn increases the ability to concentrate and stimulates the brain by increasing the action of neurotransmitters.

Caffeine has been prescribed and consumed to restore mental alertness, focus, motivation, and fatigue. Caffeine can also increase skeletal muscle performance including strength, power, and endurance. Caffeine stimulates all levels of the nervous system and speeds metabolism. The ultimate result for athletes is improved long-term consistency in training intensity. Caffeine is often considered the ultimate sports supplement as it has been shown to increase endurance by about fifteen percent by speeding the use of fat during exercise.

Flower Pollen Extract has been used by many countries to treat various conditions of ill health. It has such great acclaim that Swedish courts have acknowledged its health benefits and allow for these claims to be made legally. In many studies Flower Pollen Extract has proven to have hepatoprotective effects (promote liver health), anti-inflammatory qualities, and has been used to treat such ailments as rheumatoid arthritis and cardiovascular diseases.

Flower Pollen Extract is made up of many vitamins, carotenoids, minerals, amino acids, enzymes, and lipids. Flower Pollen Extract is directly linked to cell regeneration and claims of increased virility. Flower Pollen Extracts clinically proven antioxidant effects are extremely powerful. Antioxidants protect the cells in the body's vital organs against the harmful effects of food and the environment. Antioxidants also help its consumers fight stress and disease.

Vitamin B6 is also known as Pyridoxine. Vitamin B6 is a vitamin required for good physical and mental health. Vitamin B6 is used to process and metabolize fats, proteins, and carbohydrates. As a result, athletes may have a higher requirement for Vitamin B6 than sedentary individuals. Vitamin B6 also affects ones behavior and mood and assists in the balancing of sodium and potassium. A deficiency of this vitamin can cause nervousness, irritability, weakness, insomnia, depression, asthma, and allergies. Vitamin B6 is highly recommended to individuals using alcohol, those on a high protein diet, individuals with an overactive thyroid or intestinal diseases caused by nutritional "malabsorption", and also those who are allergic to MSG (monosodium glutamate).

White Willow Bark Extract comes from the white willow tree, *Salix Alba*. For centuries, it has been used by Chinese healers as an anti-inflammatory and fever reducer. White Willow Bark Extract is effective in relieving headaches and commonly referred to as "herbal aspirin". White Willow Bark Extract acts by lowering the body's levels of compounds called prostaglandins which cause inflammation and pain. Many studies have also shown the extract to have antioxidant and immune-boosting properties.

Sclareolide is derived from clary sage. Scalereolide is a widely used compound due to its excellent thermogenic properties and could be used to aid in weight loss and sports nutrition. It also increases thyroid hormone production, which increases the metabolism helping build lean body muscle mass and reduce body fat without the cardiovascular stimulant effect.

Thiamin also called Vitamin B1. Thiamin is very crucial in many body functions. Thiamin is known as a miraculous nutrient because it may have antioxidant and detoxification activities while also enhancing circulation and helping in the metabolism of carbohydrates. Thiamin is also purported to do wonders for the brain and has been used to boost memory and learning as well as treat depression. Thiamin was found to have positive effects on mood and cognitive functioning in a recent study of one-hundred twenty young females. When Thiamin is depleted in the body there is the probability that a person will experience muscle soreness, pain, sensitivity, and weakness. An increase in the intake of Thiamin is highly recommended for those who ingest alcohol due to the fact that alcohol interferes with the absorption of Thiamin and its storage in tissue.

Niacin is also known as Vitamin B3. Niacin is a water soluble vitamin that is needed to maintain a healthy body. The body uses Niacin in the process of releasing energy from carbohydrates. Niacin is needed to form fat from carbohydrates and to process alcohol. When consuming alcohol, it is important to increase the intake of Niacin in order to regulate the level of triglycerides. Niacin plays an important role in ridding the body of toxic and harmful chemicals. It also lowers cholesterol, helps circulation, fights depression, and eases pain from arthritis.

Pantothenic Acid, also called Vitamin B5, is sometimes referred to as the "anti-stress" vitamin because it is believed to enhance the activity of the immune system and improve the body's ability to withstand stressful conditions. It is also essential for many bodily functions such as growth, reproduction, and the production of enzymes. It aids in the breakdown of fats, carbohydrates, and proteins from foods, and turns them into useful compounds that the body needs. Pantothenic Acid also plays a crucial role in the secretion of hormones that assist the metabolism and are helpful in maintaining healthy muscles, nerves, and skin. It has putative anti-inflammatory, wound healing, and antiviral activities. Deficiency of this vitamin can result in fatigue, nausea, headaches, depression, and cardiac instability. It is recommended that people under stress that eat too many refined foods and consume alcohol, should take Vitamin B5.

The active compounds Guggulsterones E and Z are a resin from the Indian *Commiphora Mukel* tree. This resin has long been used in Ayurvedic medicine to cleanse and rejuvenate the body, especially the blood vessels and the joints. Guggulsterones E and Z were also used for digestive complaints and found to be a potentially potent anti-inflammatory compound. Guggulsterones are also reported to have pronounced antioxidant activity by protecting the important free radical scavenger enzyme SOD (Superoxide Dismutase) and keeping SOD at higher levels. In Chinese medicine, Guggulsterones is known as "mo yao" and is used to activate blood flow, relieve pain, and speed recovery.

Vitamin B12 is also known as Cyanocobalamin. Vitamin B12 is required to produce and maintain red blood cells, promote growth, and release energy. Vitamin B12 is also used to metabolize proteins, fats, and carbohydrates and to boost mental health. Deficiency in Vitamin B12 can result in fatigue, weakness, apathy, and back pain. Vitamin B12 is highly recommended for those individuals who consume alcohol because consumption of alcohol can lead to the malabsorption of Vitamin B12.

Folic Acid is a B vitamin also known as Folate or Folacin. Folic Acid can promote the regeneration of muscle tissue, skin, and bone marrow and is needed in all bodily functions that require cell division. Folic Acid is involved in amino acid metabolism as well. Folic Acid can be used to help treat Alzheimer's disease, depression, anemia, and certain types of cancer. A deficiency of Folic Acid can occur when your need for Folic Acid is increased, when dietary intake of Folic Acid is inadequate, and when your body excretes (or loses) more Folic Acid than usual. This state can occur in your body when alcohol is consumed.

Sesamin is an antioxidant. Studies show that sesamin is a functional ligan in sesame seed. Sesamin affects lipid and alcohol metabolism in the liver. Sesamin was orally administered to rats, and blood, bile and urine were collected periodically. Over 40% of the dose of sesamin was detected in bile as glucuronides of 2-(3,4-methylenedioxyphenyl)-6-(3,4-dihydroxyphenyl)-cis-dioxabicyclo [3.3.0] octane and 2-(3,4-dihydroxyphenyl)-6-(3,4-dihydroxyphenyl)-cis-dioxabicyclo [3.3.0] octane by 24 hr after administration. Antioxidant activities of these metabolites were compared and catechol metabolites showed strong radical scavenging activities against not only superoxide anion radical but also hydroxyl radical. It was suggested that sesamin was absorbed by the route of portal vein and metabolized to mono- or di-catechol metabolite by drug metabolizing enzymes in the liver cells. Both metabolites exhibited antioxidant activity in the liver and were finally conjugated with glucuronic acid and to excrete in bile. Sesamin can be classified as a pro-antioxidant. The profiles of gene expression of the liver in rats given sesamin or vehicle were compared. The gene expression levels of the late stage enzymes of beta-oxidation including trifunctional enzyme, acyl-CoA oxidase, bifunctional enzyme and 3-ketoacyl-CoA thiolase were significantly increased by sesamin. On the other hand, the transcription of the genes encoding the enzymes for fatty acid synthesis was decreased. Moreover, in sesamin rats, the gene expression of aldehyde dehydrogenase was increased about 3-fold, whereas alcohol dehydrogenase, liver catalase and CYP2E1 were not changed. These results suggested that sesamin ingestion regulated the transcription levels of hepatic metabolizing enzymes for lipids and alcohol.

Alpha-lipoic acid (ALA) is an antioxidant that is manufactured in the human body. Alpha-lipoic acid works together with other antioxidants such as vitamins C and E. ALA is important for growth, helps to prevent cell damage, and helps the body rid itself of harmful substances. Alpha-lipoic acid is thought to be useful in the treatment of chronic hepatitis because it relieves stress on the liver and helps rid the body of toxins. There have been several case reports of use of alpha-lipoic acid in combination with silymarin (milk thistle) and selenium (a substance with liver-protecting and antioxidant properties) to help treat hepatitis C (a serious type of hepatitis contracted from blood and bodily fluids that does not have an adequate cure or treatment). ALA has also been used in conjunction with silymarin to treat *Amanita* poisoning. *Amanita* is a highly poisonous mushroom that causes liver damage. Alpha-lipoic acid can be purchased in dosages ranging 30 mg to 100 mg tablets. Currently there are no established recommended doses for supplementation. For general antioxidant support, the recommended dose of ALA is 20 mg to 50 mg per day. A typical dose is one or two 50-mg capsules daily as a dietary supplement. Studies that have been successful in improving nerve function in diabetics have used 600 mg of alpha-lipoic acid per day in divided doses.

Other features which are considered as characteristic for the invention are set forth in the appended claims.

Although the invention is illustrated and described herein as embodied in a composition including superoxide dismutase and prickly-pear cactus for minimizing and preventing hangovers, it is nevertheless not intended to be limited to the details shown, since various modifications and structural changes may be made therein without departing from the spirit of the invention and within the scope and range of equivalents of the claims.

The formulation and method of delivery of the invention, however, together with additional objects and advantages thereof will be best understood from the following description of specific embodiments when read in connection with the accompanying examples.

BRIEF DESCRIPTION OF THE SEVERAL VIEWS OF THE DRAWING

Not applicable.

DETAILED DESCRIPTION OF THE INVENTION

The dietary supplement of the present invention combines *opuntia ficus indica* (Prickly Pear Cactus OFI) with Superoxide Dismutase (SOD) to provide a unique boost to the body which assists the body in efficiently metabolizing alcohol and helping to combat the symptoms commonly associated with a hangover. The dietary supplement formula can be embodied in a capsule, tablet, or liquid carrier.

In the preferred embodiment the ingredients in the table are combined in the amounts indicated.

Example 1

| INGREDIENT | WEIGHT | % OF DAILY VALUE |
| --- | --- | --- |
| Vitamin $B_6$ (as pyridoxine HCl) | 50 mg | 2.500% |
| Folate (as folic acid) | 400 mcg | 100% |
| Vitamin B12 (as cyanocobalamin) | 900 mcg | 15.000% |
| Pantothenic acid (as D-calcium pantothenate) | 20 mg | 200% |
| Superoxide dismutase (SOD) | 200 mg | * |
| Milk thistle seed extract | 150 mg | * |
| Flower pollen extract | 40 mg | * |
| Prickly pear cactus (*Opunta ficus indica*) | 800 mg | * |
| Eleuthero root extract | 200 mg | * |
| Guggulsterones E and Z | 15 mg | * |
| White willow bark extract (15% salicin) | 40 mg | * |
| Sclareolide (from clary sage) | 30 mg | * |
| *Ginkgo biloba* leaf extract (24% ginkgo flavane glycosides, 6% terpene lactones) | 100 mg | * |
| Caffeine (natural) | 80 mg | * |
| *Boswellia serrata* resin extract | 250 mg | * |

*Daily value not established

Example 2

Serving Size is four (4) capsules. Each capsule includes the following formulation.

| Ingredient | Amount per serving (mg) | Amount per Capsule (mg) | Material |
| --- | --- | --- | --- |
| Thiamine | 20 | 5 | |
| Niacin | 20 | 5 | |
| Vitamin B6 (Pyridoxine HCl) | 50 | 12.5 | |
| Folate (Folic acid) | 0.4 | 0.1 | |
| Vitamin B12 | 0.9 | 0.225 | |
| Pantothenic acid | 20 | 5 | |
| Superoxide Dismutase (SOD) | 200 | 50 | Glisodin |
| Milk thistle seed extract | 150 | 37.5 | Indena Milk thistle |
| Flower Pollen extract | 40 | 10 | Graminex ™ G63 Powder Capsule and tablet ready |
| Prickly Peak cactus leaf | 800 | 200 | |
| Eleuthero root extract | 200 | 50 | Indena Eleuthero Extract 0.8% (Huisong) |
| Guggulsterones EZ | 15 | 3.75 | Guggul EZ |
| White willow bark extract | 40 | 10 | Indena White Willow Bark Extract 15% Salicin |
| Sclareolide | 30 | 7.5 | Sclareolide |
| *Ginkgo biloba* extract | 100 | 25 | Indena *Ginkgo* (Huisong) |
| Caffeine | 80 | 20 | |
| *Boswellia serrata* extract | 250 | 62.5 | *Boswellia* |

The combination of ingredients and amounts may vary. However, the supplement must at least include a combination of OFI and SOD. In early testing, dietary supplements made according to the combination disclosed in the above-table were found to be more effective in relieving the symptoms commonly associated with hangovers following the intake of alcohol than were other dietary supplements available in the market. The dietary supplement formula of the present invention can be added or combined with other existing food and liquid supplements.

I claim:

1. A composition for protecting against, minimizing effects of, and hastening recovery from symptoms associated with an alcohol induced hangover, comprising:
   50 to 300 milligrams of superoxide dismutase (SOD); and
   250 to 2800 milligrams of prickly pear cactus.

2. The composition according to claim 1, further comprising sesamin.

3. The composition according to claim 2, wherein a daily dosage of said sesamin is from 250 to 500 milligrams.

4. The composition according to claim 1, further comprising alpha-lipoic acid.

5. The composition according to claim 4, wherein a daily dosage of said alpha-lipoic acid is from 50 to 300 milligrams.

6. The composition according to claim 1, further comprising thiamine.

7. The composition according to claim 1, further comprising niacin.

8. The composition according to claim 1, further comprising vitamin B6.

9. The composition according to claim 1, further comprising folate.

10. The composition according to claim 1, further comprising vitamin B12.

11. The composition according to claim 1, further comprising pantothenic acid.

12. The composition according to claim 1, further comprising milk thistle seed extract.

13. The composition according to claim 1, further comprising flower pollen extract.

14. The composition according to claim 1, further comprising eleuthero root extract.

15. The composition according to claim 1, further comprising guggulsterones EZ.

16. The composition according to claim 1, further comprising white willow bark extract.

17. The composition according to claim 1, further comprising sclareolide.

18. The composition according to claim 1, further comprising *ginkgo biloba* extract.

19. The composition according to claim 1, further comprising caffeine.

20. The composition according to claim 1, further comprising and *boswellia serrata* extract.

21. A composition for protecting against, minimizing effects of, and hastening recovery from symptoms associated with an alcohol induced hangover, comprising:
   superoxide dismutase (SOD), a daily dosage of said superoxide dismutase being from 50 to 300 milligrams;
   prickly pear cactus, a daily dosage of said prickly pear cactus being from 250 to 800 milligrams;
   thiamine;
   niacin;
   vitamin B6;
   folate;
   vitamin B12;
   pantothenic acid;
   milk thistle seed extract;
   flower pollen extract;
   eleuthero root extract;
   guggulsterones EZ;
   white willow bark extract;
   sclareolide;
   *ginkgo biloba* extract;
   caffeine; and
   *boswellia serrata* extract.

22. A method for protecting against, minimizing effects of, and hastening recovery from symptoms associated with an alcohol induced hangover, which comprises:
   administering a daily dosage of 50 to 300 milligrams of superoxide dismutase (SOD); and
   administering a daily dosage of 250 to 800 milligrams of prickly pear cactus.

23. The method according to claim 22, which further comprises administering white willow bark extract.

* * * * *